US012738380B2

(12) United States Patent
Mansoor et al.

(10) Patent No.: US 12,738,380 B2
(45) Date of Patent: Sep. 15, 2026

(54) COMBINING GENERALIST AND SPECIALIST MEDICAL AI FOR OPTIMIZING PERFORMANCE

(71) Applicant: Siemens Healthineers AG, Forchheim (DE)

(72) Inventors: Awais Mansoor, Potomac, MD (US); Bogdan Georgescu, Princeton, NJ (US); Florin-Cristian Ghesu, Baiersdorf (DE); Ingo Schmuecking, Yardley, PA (US); Pranjal Sahu, Morrisville, PA (US); Sasa Grbic, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 35 days.

(21) Appl. No.: 18/756,404

(22) Filed: Jun. 27, 2024

(65) Prior Publication Data

US 2026/0004932 A1 Jan. 1, 2026

(51) Int. Cl.

| | |
|---|---|
| ***G16H 50/20*** | (2018.01) |
| ***G16H 10/60*** | (2018.01) |
| ***G16H 30/40*** | (2018.01) |
| ***G16H 40/20*** | (2018.01) |

(52) U.S. Cl.

CPC ............. *G16H 50/20* (2018.01); *G16H 10/60* (2018.01); *G16H 30/40* (2018.01); *G16H 40/20* (2018.01)

(58) Field of Classification Search

None

See application file for complete search history.

(56) References Cited

U.S. PATENT DOCUMENTS

| | | | | |
|---|---|---|---|---|
| 2011/0046979 | A1* | 2/2011 | Tulipano ................ | G16H 50/20 707/E17.014 |
| 2018/0137249 | A1* | 5/2018 | Eggebraaten .......... | G16H 50/70 |
| 2021/0183485 | A1* | 6/2021 | Yao ........................ | G06V 10/25 |

(Continued)

OTHER PUBLICATIONS

Oyedeji et al. ("Design and implementation of a medical diagnostic expert system." J. Eng. Sci 10.2 (2019): 103-109) (Year: 2019).*

(Continued)

*Primary Examiner* — Christopher B Tokarczyk

(57) ABSTRACT

Systems and methods performing a medical analysis task using a GMAI (generalist medical artificial intelligence) system and an SMAI (specialist medical artificial intelligence) system are provided. Patient data is received. Using a GMAI (generalist medical artificial intelligence) system, 1) a medical analysis task is performed on the patient data and 2) an uncertainty associated with results of the medical analysis task performed using the GMAI system is determined. It is determined whether the uncertainty associated with the results of the medical analysis task performed using the GMAI system is satisfactory. In response to determining that the uncertainty associated with the results of the medical analysis task performed using the GMAI system is not satisfactory, the medical analysis task is performed on the patient data using an SMAI (specialist medical artificial intelligence) system. Results of the medical analysis task performed using the SMAI system are output.

18 Claims, 8 Drawing Sheets

(56) References Cited

U.S. PATENT DOCUMENTS

2023/0336340 A1 * 10/2023 Polleri ................ G06F 11/3466

OTHER PUBLICATIONS

Ghesu et al., "Quantifying and leveraging predictive uncertainty for medical image assessment", arXiv:2007.04258v1, 2020, pp. 1-28.

Moor et al., "Foundation models for generalist medical artificial intelligence", Nature, 2023, pp. 259-265.

* cited by examiner

Figure 1:
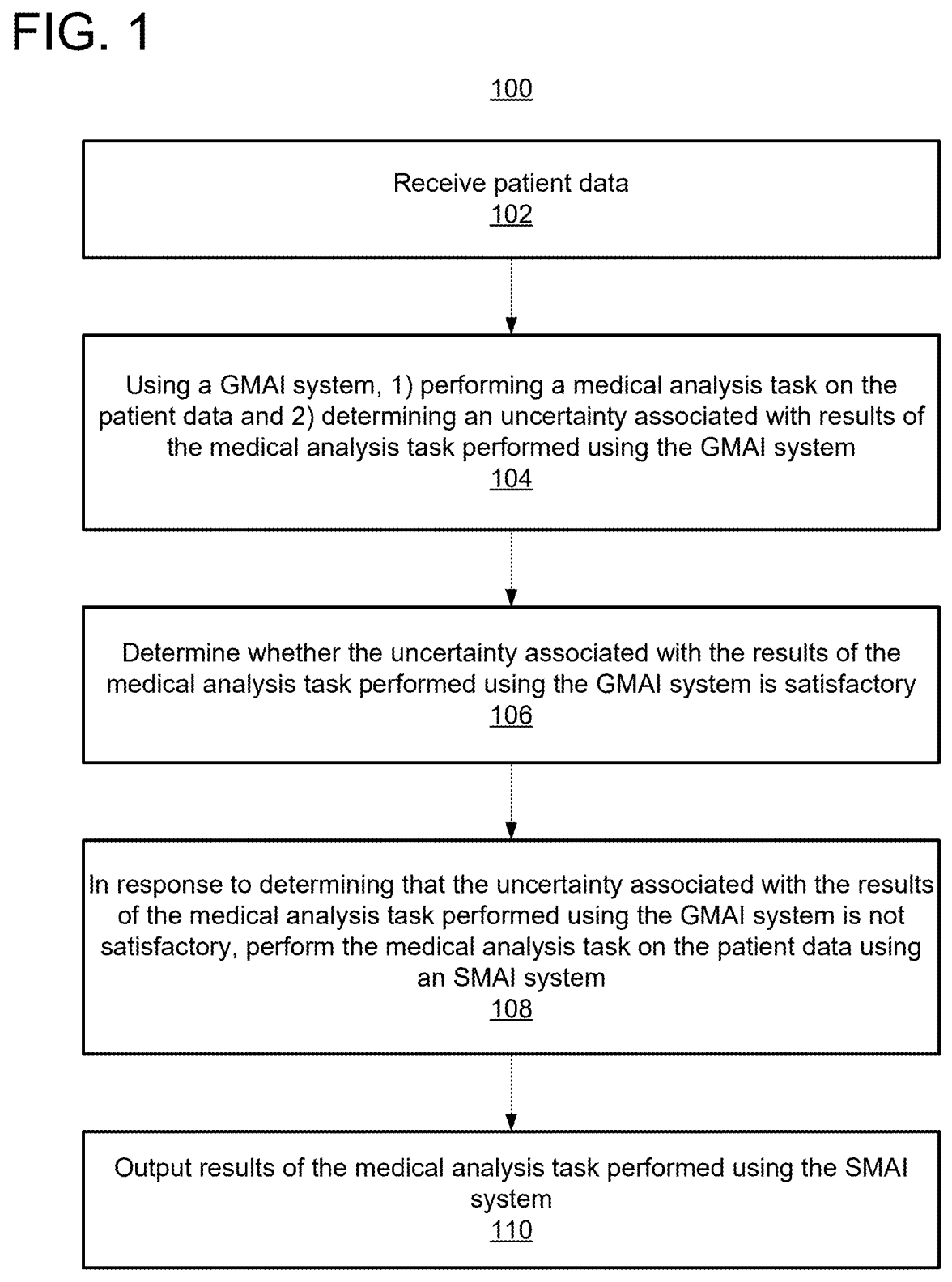

Receive patient data
102

Using a GMAI system, 1) performing a medical analysis task on the patient data and 2) determining an uncertainty associated with results of the medical analysis task performed using the GMAI system
104

Determine whether the uncertainty associated with the results of the medical analysis task performed using the GMAI system is satisfactory
106

In response to determining that the uncertainty associated with the results of the medical analysis task performed using the GMAI system is not satisfactory, perform the medical analysis task on the patient data using an SMAI system
108

Output results of the medical analysis task performed using the SMAI system
110

COMBINING GENERALIST AND SPECIALIST MEDICAL AI FOR OPTIMIZING PERFORMANCE

TECHNICAL FIELD

The present invention relates generally to generalist and specialist medical AI (artificial intelligence), and in particular to combining generalist and specialist medical AI for optimizing performance.

BACKGROUND

Specialist medical AI (SMAI) systems are trained to perform specific medical tasks with a high level of performance. However, scaling and optimizing SMAI systems to expert-grade performance is limited by the large amounts of curated training data required to train such SMAI systems. Further, complexity and cost of annotating such large amounts of curated training data increases due to the need to specifically delineate findings in the training data. There is thus a significant cost in curating and annotating training data at a very large scale to achieve robust high-performance of SMAI systems.

Generalist medical AI (GMAI) systems are trained to perform a broad range of medical tasks across various medical domains. GMAI systems are typically trained on massive, diverse datasets with little to no annotations. While GMAI systems are easier to train, cheaper, and more efficient, performance of GMAI systems is not currently at par with SMAI systems. GMAI systems perform competitively for simplistic medical scenarios but are severely outperformed by SMAI systems on challenging and rare medical scenarios.

BRIEF SUMMARY OF THE INVENTION

In accordance with one or more embodiments, systems and methods performing a medical analysis task using a GMAI (generalist medical artificial intelligence) system and an SMAI (specialist medical artificial intelligence) system are provided. Patient data is received. Using a GMAI (generalist medical artificial intelligence) system, 1) a medical analysis task is performed on the patient data and 2) an uncertainty associated with results of the medical analysis task performed using the GMAI system is determined. It is determined whether the uncertainty associated with the results of the medical analysis task performed using the GMAI system is satisfactory. In response to determining that the uncertainty associated with the results of the medical analysis task performed using the GMAI system is not satisfactory, the medical analysis task is performed on the patient data using an SMAI (specialist medical artificial intelligence) system. Results of the medical analysis task performed using the SMAI system are output.

In one embodiment, it is determined whether the uncertainty associated with the results of the medical analysis task performed using the GMAI system is satisfactory by comparing the uncertainty to one or more threshold values and determining whether the uncertainty is satisfactory based on the comparison.

In one embodiment, it is determined whether the uncertainty associated with the results of the medical analysis task performed using the GMAI system is satisfactory using a lookup table.

In one embodiment, a prompt comprising instructions for performing the medical analysis task is received. The medical analysis task is performed on the patient data using the GMAI system based on the prompt.

In one embodiment, in response to determining that the results of the medical analysis task performed by the GMAI system is satisfactory, the results of the medical analysis task performed by the GMAI system are output.

In one embodiment, the patient data comprises a current imaging study and a prior imaging study and the medical analysis task comprises analyzing changes between the current imaging study and the prior imaging study.

In one embodiment, the GMAI system comprises a language model.

In one embodiment, the medical analysis task comprises detection of nodules in a chest x-ray image of the patient.

In one embodiment, the patient data comprises one or more medical images of the patient and text-based data of the patient.

These and other advantages of the invention will be apparent to those of ordinary skill in the art by reference to the following detailed description and the accompanying drawings.

BRIEF DESCRIPTION OF THE DRAWINGS

FIG. 1 shows a method for performing a medical analysis task using a GMAI system and an SMAI system, in accordance with one or more embodiments;

DETAILED DESCRIPTION

The present invention generally relates to methods and systems for combining generalist and specialist medical AI for optimizing performance. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for combining the high-performance gains provided by SMAI systems with the efficiency of task provided by GMAI systems. In one embodiment, a GMAI system is used for general cases and an SMAI system is used for a very small set of challenging edge cases. For example, for chest x-ray lesion/nodule detection, nodules that are clearly visible will be analyzed by the GMAI system while nodules having out-of-distribution characteristics (e.g., very subtle or oddly shaped nodules) will be analyzed by the SMAI system. Advantageously, the SMAI system will only be required to be trained on curated data for the out-of-distribution characteristics. Embodiments described herein thus provide for cost savings, rapid scaling, and efficiency gains.

Figure 2:
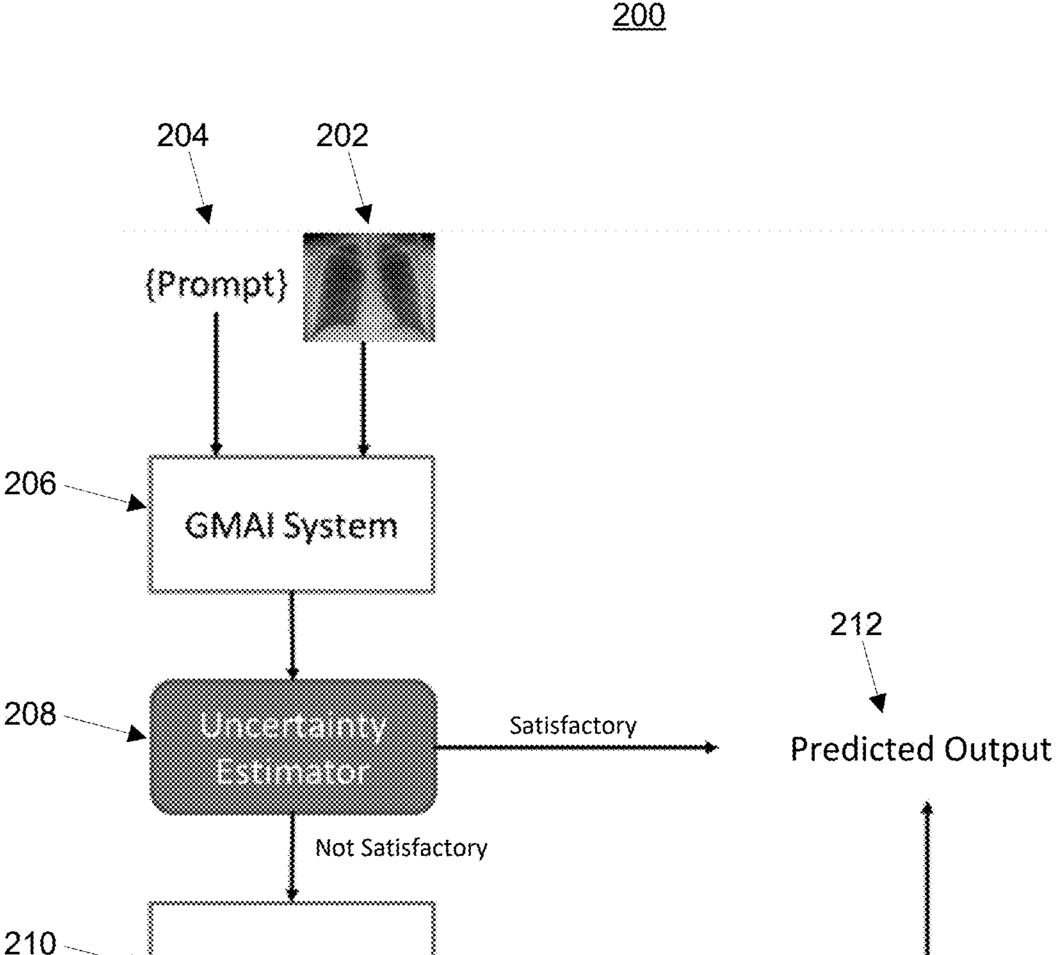
FIG. 2 shows a workflow for performing a medical analysis task using a GMAI system and an SMAI system, in accordance with one or more embodiments.

FIG. 1 shows a method 100 for performing a medical analysis task using a GMAI system and an SMAI system, in accordance with one or more embodiments. The steps and sub-steps of method 100 may be performed by one or more suitable computing devices, such as, e.g., computer 802 of FIG. 8. FIG. 2 shows a workflow 200 for performing a medical analysis task using a GMAI system and an SMAI system, in accordance with one or more embodiments. FIG. 1 and FIG. 2 will be described together.

At step 102 of FIG. 1, patient data is received. The patient data may comprise any suitable data relating to a patient.

In one embodiment, the patient data comprises one or more medical images depicting an anatomical object or objects of interest of the patient (e.g., organs, vessels, bones, lesions/nodules/tumors, other abnormalities, etc.). In one example, as shown in workflow 200 of FIG. 2, the one or more medical images is medical image 202. In one embodiment, the one or more medical images may comprise x-ray images of the chest of the patient. However, the one or more medical images may be of any other suitable modality, such as, e.g., MRI (magnetic resonance imaging), CT (computed tomography), US (ultrasound), or any other medical imaging modality or combinations of medical imaging modalities. The one or more medical images may be 2D (two dimensional) images and/or 3D (three dimensional) volumes, and may comprise a single input medical image or a plurality of input medical images.

In one embodiment, the patient data comprises text-based patient data. For example, the text-based patient data may comprise medical reports of the patient (e.g., radiology reports or clinical reports). However, the text-based patient data may comprise any other suitable text-based data of the patient, such as, e.g., demographic information, vital signs, medical history, family history, laboratory results, clinical contexts, measurements and information extracted from medical images, etc. of the patient.

Figure 7:
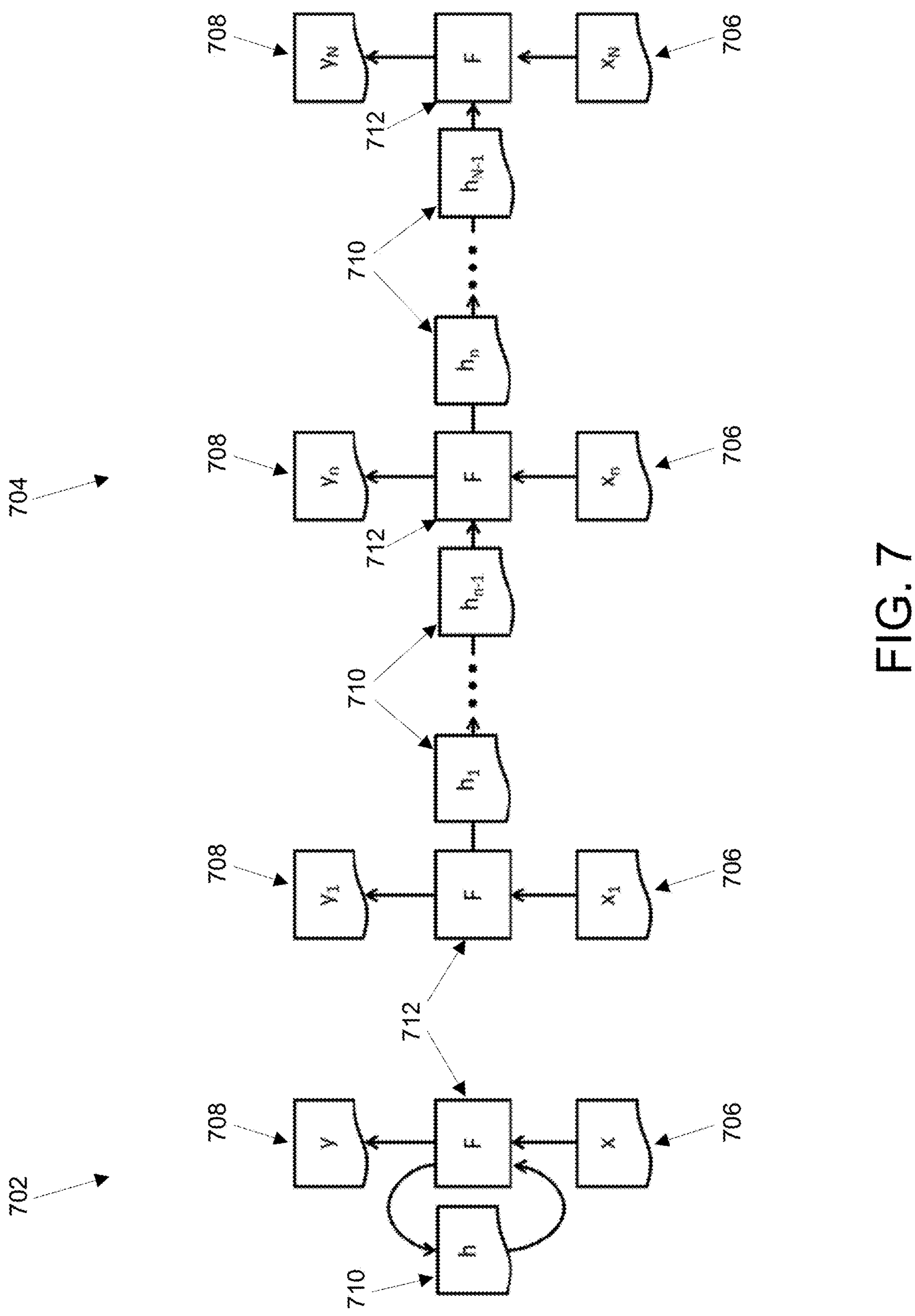
FIG. 7 shows a schematic structure of a recurrent machine learning model that may be used to implement one or more embodiments.

The patient data may be received, for example, by directly receiving the one or more medical images from the image acquisition device (e.g., image acquisition device 814 of FIG. 8) as the medical images are acquired, by loading the patient data from a storage or memory of a computer system (e.g., storage 812 or memory 810 of computer 802 of FIG. 8), or by receiving the patient data from a remote computer system (e.g., computer 702 of FIG. 7). Such a computer system or remote computer system may comprise one or more patient databases, such as, e.g., an EHR (electronic health record), EMR (electronic medical record), PHR (personal health record), HIS (health information system), RIS (radiology information system), PACS (picture archiving and communication system), LIMS (laboratory information management system), or any other suitable database or system.

In one embodiment, a prompt for performing a medical analysis task is also received at step 102 of FIG. 1. In one example, as shown in workflow 200 of FIG. 2, the prompt is prompt 204. A prompt refers to input to a language model and may comprise instructions for performing the medical analysis task. The prompt may be received, for example, from a computer system via one or more APIs (application programming interfaces) or from a user interacting with a computer system (e.g., computer 802 of FIG. 8).

At step 104 of FIG. 1, using a GMAI system, 1) a medical analysis task is performed on the patient data and 2) an uncertainty associated with results of the medical analysis task performed using the GMAI system is determined. In one example, as shown in workflow 200 of FIG. 2, the GMAI system is GMAI system 206. The medical analysis task may be, for example, detection of nodules in a chest x-ray of a patient. However, the medical analysis task may be any other suitable task performed on the patient data, such as, e.g., detection, classification, segmentation, quantification, diagnosis, etc.

A GMAI system is an AI system trained to perform a broad range of medical analysis tasks across various medical domains, rather than being specialized for a particular task or medical domain. The GMAI system receives as input 1) the patient data and 2) (optionally) the prompt. The GMAI system generates as output 1) results of the medical analysis task performed on the patient data according to the prompt and 2) an uncertainty associated with the results of the medical analysis task performed using the GMAI system.

The uncertainty reflects a measure of the confidence of the GMAI system in predicting the results of the medical analysis task. The uncertainty may quantify any number of attributes contributing to the uncertainty, such as, e.g., challenging or subtle cases, image quality, diagnosis, lack of knowledge of the GMAI system (e.g., whether the patient data is out-of-distribution on the training data on which the GMAI system was trained), etc. The uncertainty may be generated by the GMAI system in response to the prompt. For example, the prompt may comprise instructions instructing the GMAI system to generate the uncertainty associated with the results of the medical analysis task. The instructions may also define the format the uncertainty is to be represented. In one example, the uncertainty may be represented as a number between zero and one. In another example, the uncertainty may be represented as a cost function representing a plurality of measures of uncertainty to represent each of the aspects of uncertainty. However, the uncertainty may be represented in any other suitable format.

The GMAI system may be implemented according to any suitable AI or ML (machine learning) based model. In one embodiment, the GMAI system may be implemented using a language model, which may be a multi-modal language model integrating images, text, audio, and/or other types of data. The language model may be an LLM (large language model), which may be implemented using any suitable pretrained deep learning based LLM. For example, the LLM may be based on the transformer architecture, which uses an attention mechanism to capture long-range dependencies in text. One example of a transformer-based architecture is GPT (generative pre-training transformer), which has a multilayer transformer decoder architecture that may be pretrained to optimize the next token prediction task and then fine-tuned with labelled data for various downstream tasks. Other exemplary transformer-based architectures include BLOOM (BigScience Large Open-science Open-access Multilingual Language Model) and BERT (Bidirectional Encoder Representations from Transformers). The LLM may be fine-tuned for optimizing performance for the medical domain. The language model may be any other suitable language model. For example, the language model may be a small language model, which uses a relatively smaller neural network, has fewer parameters, and is trained on less training data as compared with an LLM.

In one embodiment, the GMAI system may additionally or alternatively be implemented using one or more different types of neural networks, such as, e.g., CNNs (convolutional neural networks), RNNs (recurrent neural networks), FNNs (feedforward neural networks), etc.

The GMAI system is trained during a prior offline or training stage. In one embodiment, the GMAI system may be trained according to workflow 300 of FIG. 3, described in further detail below. Once trained, the trained GMAI system is applied during an online or inference stage, e.g., to perform step 104 of FIG. 1.

At step 106 of FIG. 1, it is determined whether the uncertainty associated with the results of the medical analysis task performed using the GMAI system is satisfactory. In one example, as shown in workflow 200 of FIG. 2, uncertainty estimator 208 determines whether the uncertainty associated with the results of the medical analysis task performed using the GMAI system is satisfactory. It may be determined whether the uncertainty associated with the results of the medical analysis task performed using the GMAI system is satisfactory using any suitable approach.

In one embodiment, it is determined whether the uncertainty associated with the results of the medical analysis task performed using the GMAI system is satisfactory by comparing the uncertainty to one or more threshold values. It is determined whether the uncertainty associated with the results of the medical analysis task performed using the GMAI system is satisfactory based on the comparison. For example, the uncertainty may be satisfactory where the uncertainty is less than the threshold but unsatisfactory where the uncertainty is greater than or equal to the threshold.

In another embodiment, it is determined whether the uncertainty associated with the results of the medical analysis task performed using the GMAI system is satisfactory by using a lookup table. For example, if the results of the medical analysis task comprise a diagnosis and the lookup table indicates that the diagnosis is not satisfactory, it is determined that the uncertainty associated with the results of the medical analysis task performed using the GMAI system is not satisfactory.

At step 108 of FIG. 1, in response to determining that the uncertainty associated with the results of the medical analysis task performed using the GMAI system is not satisfactory, the medical analysis task is performed on the patient data using an SMAI system. In one example, as shown in workflow 200 of FIG. 2, the SMAI system is SMAI system 2010.

An SMAI system is an AI system trained to perform a specific medical analysis task. Unlike the GMAI system, the SMAI system is optimized for high performance for a specific medical analysis task. The SMAI receives as input the patient data and generates as output results of the medical analysis task performed on the patient data. In one embodiment, the SMAI system is implemented as a dedicated CNN, such as, e.g., VGG (visual geometry group) very deep convolutional network, ResNet (residual network), DenseNet (dense convolutional network), U-Net, etc. However, the SMAI system may be implemented according to any other suitable AI or ML based model.

The SMAI system is trained during a prior offline or training stage. In one embodiment, the SMAI system may be trained according to workflow 400 of FIG. 4, described in further detail below. Once trained, the trained SMAI system is applied during an online or inference stage, e.g., to perform step 108 of FIG. 1.

At step 110 of FIG. 1, results of the medical analysis task performed using the SMAI system are output. In one example, as shown in workflow 200 of FIG. 2, results of the medical analysis task performed using SMAI system 210 are output as predicted output 212. The results of the medical analysis task performed using the SMAI system can be output by, for example, storing the results on a memory or storage of a computer system (e.g., memory 810 or storage 812 of computer 802 of FIG. 8) or by transmitting the results to a remote computer system (e.g., computer 802 of FIG. 8).

In one embodiment, in response to determining that the uncertainty associated with the results of the medical analysis task performed using the GMAI system is satisfactory, the results of the medical analysis task performed using the GMAI system is output. In one example, as shown in workflow 200 of FIG. 2, in response to uncertainty estimator 208 determining that the uncertainty associated with the results of the medical analysis task performed using GMAI system 206 is satisfactory, the results of the medical analysis task performed using GMAI system 206 are output as predicted output 212. The results of the medical analysis task performed using the GMAI system may be output, for example, as described above with respect to the results of the medical analysis task performed using the SMAI system.

In one embodiment, the patient data comprises current and prior imaging studies (comprising medical images and procedure reports) of the patient. Method 100 of FIG. 1 is performed for the medical analysis task of analyzing changes between the current and prior imaging studies.

Figure 3:
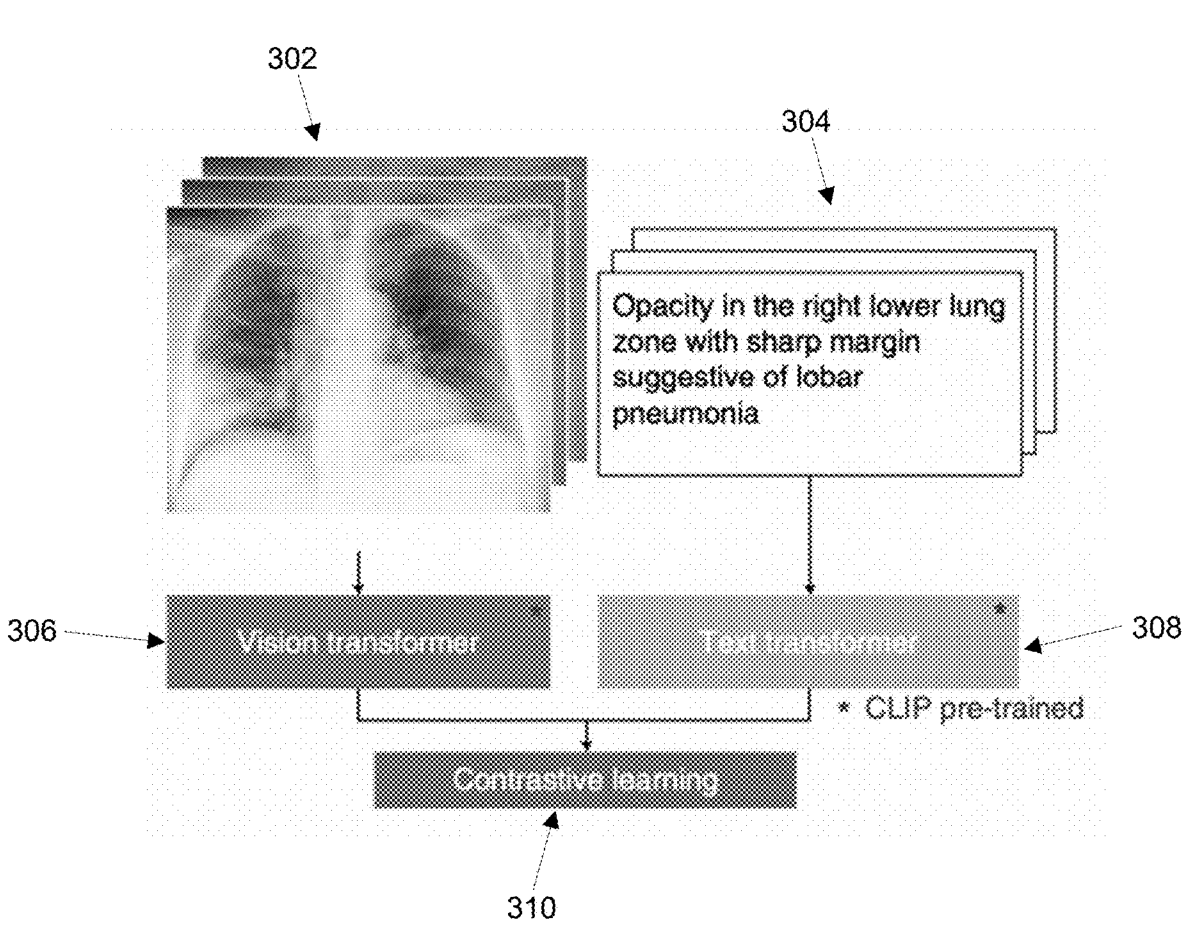
FIG. 3 shows a workflow for training a GMAI system, in accordance with one or more embodiments.

FIG. 3 shows a workflow 300 for training a GMAI system, in accordance with one or more embodiments. Workflow 300 is performed during a prior offline or training stage for training the GMAI system. Once trained, the trained GMAI system is applied during an online or inference stage, e.g., to perform step 104 of FIG. 1 or as GMAI system 206 of FIG. 2.

As shown in workflow 300, the GMAI system is implemented as a self-supervised learning model comprising vision transformer 306 and text transformer 308. In the example shown in workflow 300, vision transformer 306 and text transformer 308 form a CLIP (contrastive learning-image pre-training) pretrained neural network. Vision transformer 306 and text transformer 308 are trained on a large repository of training medical images 302 and corresponding text-based data 304 using contrastive learning 310. In some embodiment, vision transformer 306 and text transformer 308 are trained with multi-task learning to perform a plurality of different medical analysis tasks.

Figure 4:
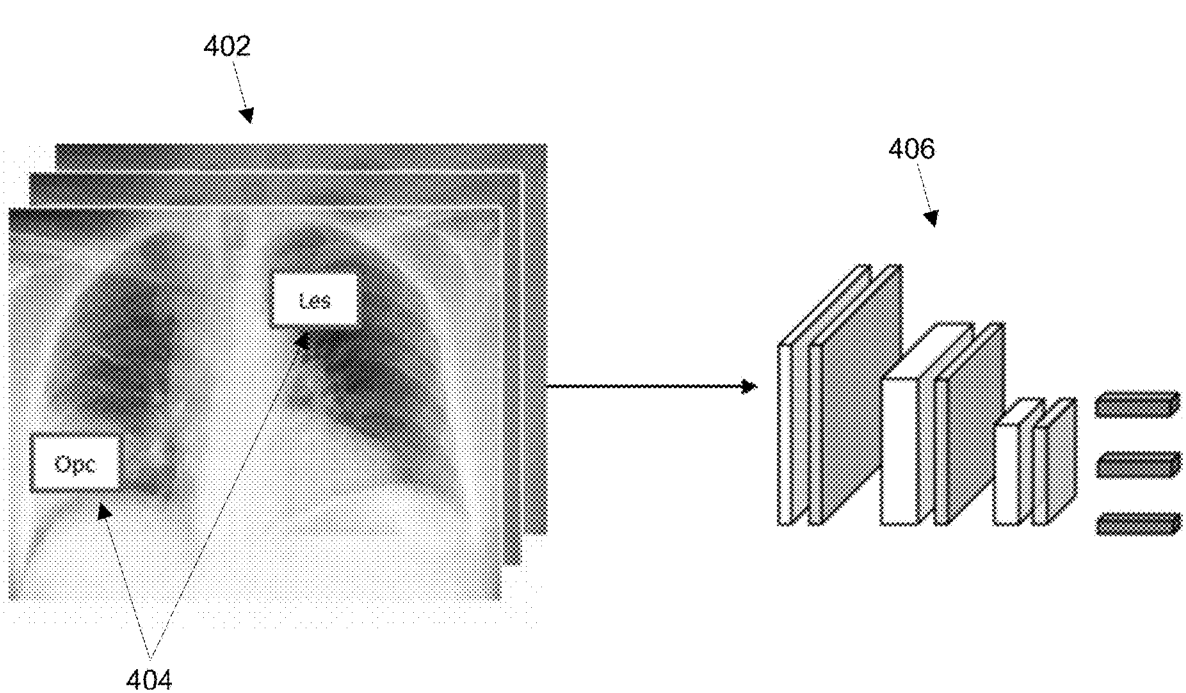
FIG. 4 shows a workflow for training an SMAI system, in accordance with one or more embodiments.

FIG. 4 shows a workflow 400 for training an SMAI system, in accordance with one or more embodiments. Workflow 400 is performed during a prior offline or training stage for training the SMAI system. Once trained, the trained SMAI system is applied during an online or inference stage, e.g., to perform step 108 of FIG. 1 or as SMAI system 210 of FIG. 2.

As shown in workflow 400, SMAI system is implemented as a dedicated CNN 406 trained with a curated repository of training medical images 402 with annotations 404. CNN 406 is trained via supervised learning using any suitable loss function, such as, e.g., cross-entropy loss or mean squared error. Advantageously, SMAI system is only trained on the challenging/edge cases where the GMAI system would fail.

Embodiments described herein are described with respect to the claimed systems as well as with respect to the claimed methods. Features, advantages or alternative embodiments herein can be assigned to the other claimed objects and vice versa. In other words, claims and embodiments for the systems can be improved with features described or claimed in the context of the respective methods. In this case, the functional features of the method are implemented by physical units of the system.

Furthermore, certain embodiments described herein are described with respect to methods and systems utilizing trained machine learning models, as well as with respect to methods and systems for providing trained machine learning models. Features, advantages or alternative embodiments herein can be assigned to the other claimed objects and vice versa. In other words, claims and embodiments for providing trained machine learning models can be improved with features described or claimed in the context of utilizing trained machine learning models, and vice versa. In particular, datasets used in the methods and systems for utilizing trained machine learning models can have the same properties and features as the corresponding datasets used in the methods and systems for providing trained machine learning models, and the trained machine learning models provided by the respective methods and systems can be used in the methods and systems for utilizing the trained machine learning models.

In general, a trained machine learning model mimics cognitive functions that humans associate with other human minds. In particular, by training based on training data the machine learning model is able to adapt to new circumstances and to detect and extrapolate patterns. Another term for "trained machine learning model" is "trained function."

In general, parameters of a machine learning model can be adapted by means of training. In particular, supervised training, semi-supervised training, unsupervised training, reinforcement learning and/or active learning can be used. Furthermore, representation learning (an alternative term is "feature learning") can be used. In particular, the parameters of the machine learning models can be adapted iteratively by several steps of training. In particular, within the training a certain cost function can be minimized. In particular, within the training of a neural network the backpropagation algorithm can be used.

In particular, a machine learning model, such as, e.g., the GMAI system of step 104 and the SMAI system of step 108 of FIG. 1, GMAI system 206 and SMAI system 210 of FIG. 2, vision transformer 306 and text transformer 308 of FIG. 3, and CNN 406 of FIG. 4, can comprise, for example, a neural network, a support vector machine, a decision tree and/or a Bayesian network, and/or the machine learning model can be based on, for example, k-means clustering, Q-learning, genetic algorithms and/or association rules. In particular, a neural network can be, e.g., a deep neural network, a convolutional neural network or a convolutional deep neural network. Furthermore, a neural network can be, e.g., an adversarial network, a deep adversarial network and/or a generative adversarial network.

Figure 5:
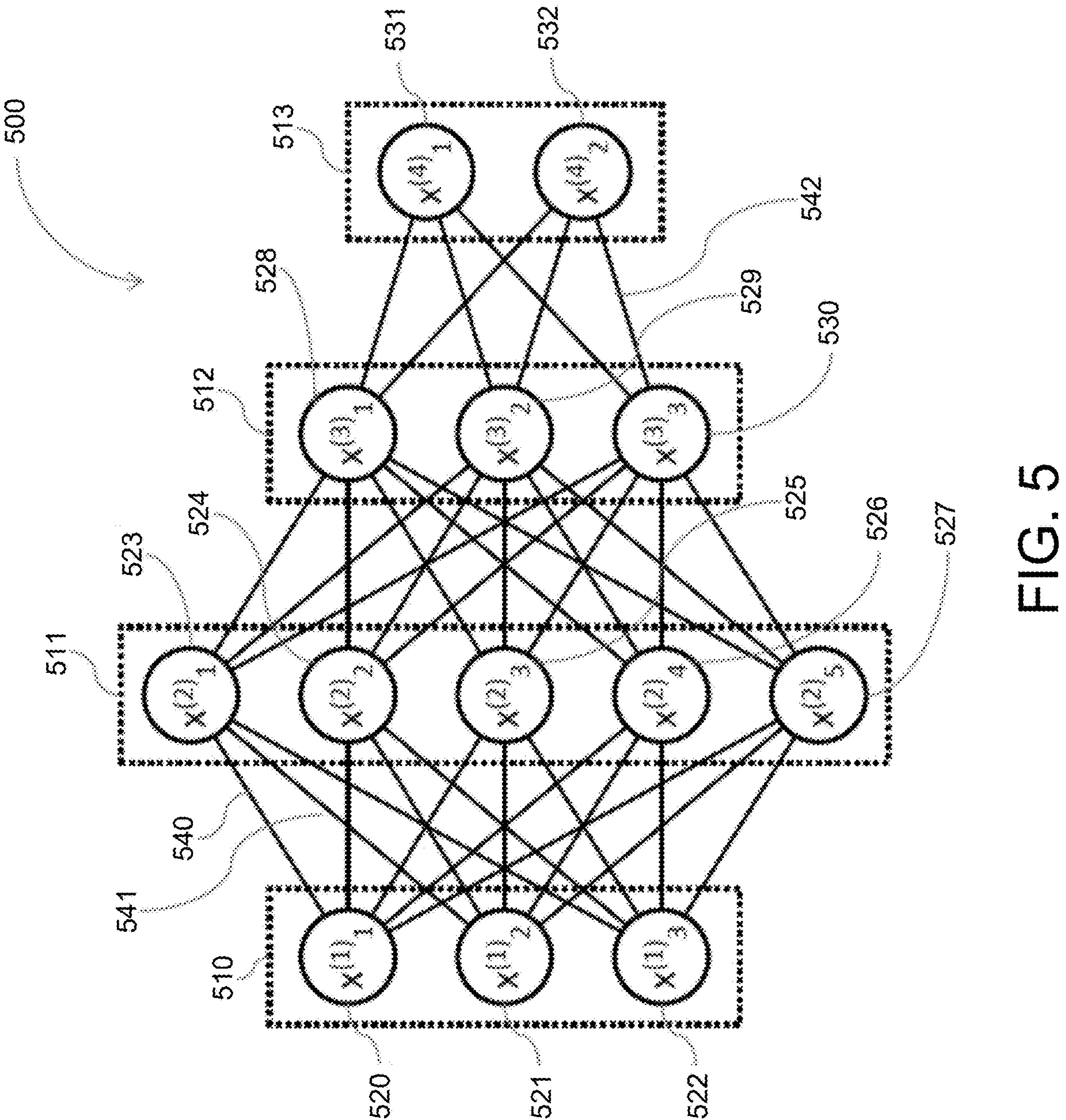
FIG. 5 shows an exemplary artificial neural network that may be used to implement one or more embodiments.

FIG. 5 shows an embodiment of an artificial neural network 500 that may be used to implement one or more machine learning models described herein. Alternative terms for "artificial neural network" are "neural network", "artificial neural net" or "neural net".

The artificial neural network 500 comprises nodes 520, . . . , 532 and edges 540, . . . 542, wherein each edge 540, . . . , 542 is a directed connection from a first node 520, . . . , 532 to a second node 520, . . . , 532. In general, the first node 520, . . . , 532 and the second node 520, . . . , 532 are different nodes 520, . . . , 532, it is also possible that the first node 520, . . . , 532 and the second node 520, . . . , 532 are identical. For example, in FIG. 5 the edge 540 is a directed connection from the node 520 to the node 523, and the edge 542 is a directed connection from the node 530 to the node 532. An edge 540, . . . , 542 from a first node 520, . . . , 532 to a second node 520, . . . , 532 is also denoted as "ingoing edge" for the second node 520, . . . , 532 and as "outgoing edge" for the first node 520, . . . , 532.

In this embodiment, the nodes 520, . . . , 532 of the artificial neural network 500 can be arranged in layers 510, . . . , 513, wherein the layers can comprise an intrinsic order introduced by the edges 540, . . . , 542 between the nodes 520, . . . , 532. In particular, edges 540, . . . , 542 can exist only between neighboring layers of nodes. In the displayed embodiment, there is an input layer 510 comprising only nodes 520, . . . , 522 without an incoming edge, an output layer 513 comprising only nodes 531, 532 without outgoing edges, and hidden layers 511, 512 in-between the input layer 510 and the output layer 513. In general, the number of hidden layers 511, 512 can be chosen arbitrarily. The number of nodes 520, . . . , 522 within the input layer 510 usually relates to the number of input values of the neural network, and the number of nodes 531, 532 within the output layer 513 usually relates to the number of output values of the neural network.

In particular, a (real) number can be assigned as a value to every node 520, . . . , 532 of the neural network 500. Here, $x^{(n)}_i$ denotes the value of the i-th node 520, . . . , 532 of the n-th layer 510, . . . , 513. The values of the nodes 520, . . . , 522 of the input layer 510 are equivalent to the input values of the neural network 500, the values of the nodes 531, 532 of the output layer 513 are equivalent to the output value of the neural network 500. Furthermore, each edge 540, . . . , 542 can comprise a weight being a real number, in particular, the weight is a real number within the interval [−1, 1] or within the interval [0, 1]. Here, $w^{(m,n)}_{i,j}$ denotes the weight of the edge between the i-th node 520, . . . , 532 of the m-th layer 510, . . . , 513 and the j-th node 520, . . . , 532 of the n-th layer 510, . . . , 513. Furthermore, the abbreviation $w^{(n)}_{i,j}$ is defined for the weight $w^{(n,n+1)}_{i,j}$.

In particular, to calculate the output values of the neural network 500, the input values are propagated through the neural network. In particular, the values of the nodes 520, . . . , 532 of the (n+1)-th layer 510, . . . , 513 can be calculated based on the values of the nodes 520, . . . , 532 of the n-th layer 510, . . . , 513 by $$x^{(n+1)}{}_j = f\left(\sum_i x^{(n)}{}_i \cdot w^{(n)}{}_{i,j}\right).$$

Herein, the function f is a transfer function (another term is "activation function"). Known transfer functions are step functions, sigmoid function (e.g., the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 510 are given by the input of the neural network 500, wherein values of the first hid-den layer 511 can be calculated based on the values of the input layer 510 of the neural network, wherein values of the second hidden layer 512 can be calculated based in the values of the first hidden layer 511, etc.

In order to set the values $w^{(m,n)}{}_{i,j}$ for the edges, the neural network 500 has to be trained using training data. In particular, training data comprises training input data and training output data (denoted as $t_i$). For a training step, the neural network 500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 500 (backpropagation algorithm). In particular, the weights are changed according to $$w'^{(n)}{}_{i,j} = w^{(n)}{}_{i,j} - \gamma \cdot \delta^{(n)}{}_j \cdot x^{(n)}{}_i$$

wherein $\gamma$ is a learning rate, and the numbers $\delta^{(n)}{}_j$ can be recursively calculated as $$\delta^{(n)}{}_j = \left(\sum_k \delta^{(n+1)}{}_k \cdot w^{(n+1)}{}_{j,k}\right) \cdot f'\left(\sum_i x^{(n)}{}_i \cdot w^{(n)}{}_{i,j}\right)$$

based on $\delta^{(n+1)}{}_j$, if the (n+1)-th layer is not the output layer, and $$\delta^{(n)}{}_j = \left(x^{(n+1)}{}_j - t^{(n+1)}{}_j\right) \cdot f'\left(x^{(n)}{}_i \cdot w^{(n)}{}_{i,j}\right)$$

if the (n+1)-th layer is the output layer 513, wherein f' is the first derivative of the activation function, and $t^{(n+1)}{}_j$ is the comparison training value for the j-th node of the output layer 513.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data/image, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

By using convolutional neural networks input images can be processed in a very efficient way, because a convolution operation based on different kernels can extract various image features, so that by adapting the weights of the convolution kernel the relevant image features can be found during training. Furthermore, based on the weight-sharing in the convolutional kernels less parameters need to be trained, which prevents overfitting in the training phase and allows to have faster training or more layers in the network, improving the performance of the network.

Figure 6:
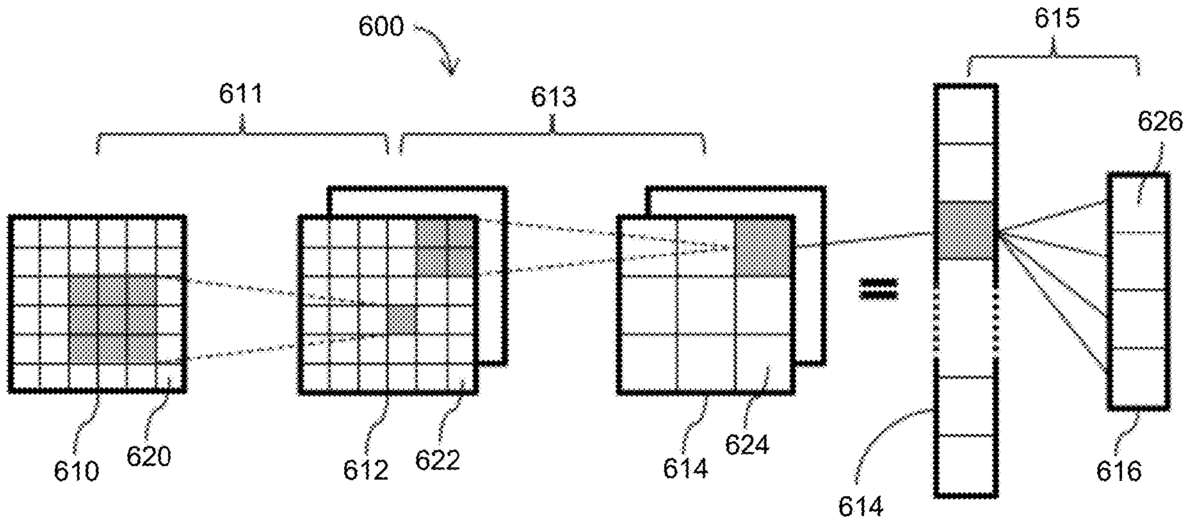
FIG. 6 shows a convolutional neural network that may be used to implement one or more embodiments.

FIG. 6 shows an embodiment of a convolutional neural network 600 that may be used to implement one or more machine learning models described herein. In the displayed embodiment, the convolutional neural network comprises 600 an input node layer 610, a convolutional layer 611, a pooling layer 613, a fully connected layer 614 and an output node layer 616, as well as hidden node layers 612, 614. Alternatively, the convolutional neural network 600 can comprise several convolutional layers 611, several pooling layers 613 and several fully connected layers 615, as well as other types of layers. The order of the layers can be chosen arbitrarily, usually fully connected layers 615 are used as the last layers before the output layer 616.

In particular, within a convolutional neural network 600 nodes 620, 622, 624 of a node layer 610, 612, 614 can be considered to be arranged as a d-dimensional matrix or as a d-dimensional image. In particular, in the two-dimensional case the value of the node 620, 622, 624 indexed with i and j in the n-th node layer 610, 612, 614 can be denoted as x(n)[i, j]. However, the arrangement of the nodes 620, 622, 624 of one node layer 610, 612, 614 does not have an effect on the calculations executed within the convolutional neural network 600 as such, since these are given solely by the structure and the weights of the edges.

A convolutional layer 611 is a connection layer between an anterior node layer 610 (with node values x(n−1)) and a posterior node layer 612 (with node values x(n)). In particular, a convolutional layer 611 is characterized by the structure and the weights of the incoming edges forming a convolution operation based on a certain number of kernels. In particular, the structure and the weights of the edges of the convolutional layer 611 are chosen such that the values x(n) of the nodes 622 of the posterior node layer 612 are calculated as a convolution x(n)=K*x(n−1) based on the values x(n−1) of the nodes 620 anterior node layer 610, where the convolution * is defined in the two-dimensional case as $$x_k^{(n)}[i, j] = (K * x^{(n-1)})[i, j] = \sum_{i'} \sum_{j'} K\,[i', j'] \cdot x^{(n-1)}[i - i', j - j'].$$

Here the kernel K is a d-dimensional matrix (in this embodiment, a two-dimensional matrix), which is usually small compared to the number of nodes 620, 622 (e.g., a 3×3 matrix, or a 5×5 matrix). In particular, this implies that the weights of the edges in the convolution layer 611 are not independent, but chosen such that they produce said convolution equation. In particular, for a kernel being a 3×3 matrix, there are only 9 independent weights (each entry of the kernel matrix corresponding to one independent weight), irrespectively of the number of nodes 620, 622 in the anterior node layer 610 and the posterior node layer 612.

In general, convolutional neural networks 600 use node layers 610, 612, 614 with a plurality of channels, in particular, due to the use of a plurality of kernels in convolutional layers 611. In those cases, the node layers can be considered as (d+1)-dimensional matrices (the first dimension indexing the channels). The action of a convolutional layer 611 is then a two-dimensional example defined as $$x^{(n)}{}_b[i, j] = \sum_a K_{a,b} * x^{(n-1)}{}_a[i, j] = \sum_a \sum_{i'} \sum_{j'} K_{a,b}[i', j'] \cdot x^{(n-1)}{}_a[i - i', j - j']$$

where $x^{(n-1)}{}_a$ corresponds to the a-th channel of the anterior node layer 610, $x^{(n)}{}_b$ corresponds to the b-th channel of the posterior node layer 612 and $K_{a,b}$ corresponds to one of the kernels. If a convolutional layer 611 acts on an anterior node layer 610 with A channels and outputs a posterior node layer 612 with B channels, there are A·B independent d-dimensional kernels $K_{a,b}$.

In general, in convolutional neural networks 600 activation functions are used. In this embodiment re ReLU (acronym for "Rectified Linear Units") is used, with R (z)=max (0, z), so that the action of the convolutional layer 611 in the two-dimensional example is $$x^{(n)_b}[i, j] = R\left(\sum_a \left(K_{a,b} * x^{(n-1)_a}\right)[i, j]\right) = R\left(\sum_a \sum_{i'} \sum_{j'} K_{a,b}[i', j'] \cdot x^{(n-1)_a}[i - i', j - j']\right)$$

It is also possible to use other activation functions, e.g., ELU (acronym for "Exponential Linear Unit"), LeakyReLU, Sigmoid, Tanh or Softmax.

In the displayed embodiment, the input layer 610 comprises 36 nodes 620, arranged as a two-dimensional 6×6 matrix. The first hidden node layer 612 comprises 72 nodes 622, arranged as two two-dimensional 6×6 matrices, each of the two matrices being the result of a convolution of the values of the input layer with a 3×3 kernel within the convolutional layer 611. Equivalently, the nodes 622 of the first hidden node layer 612 can be interpreted as arranged as a three-dimensional 2×6×6 matrix, wherein the first dimension correspond to the channel dimension.

The advantage of using convolutional layers 611 is that spatially local correlation of the input data can exploited by enforcing a local connectivity pattern between nodes of adjacent layers, in particular by each node being connected to only a small region of the nodes of the preceding layer.

A pooling layer 613 is a connection layer between an anterior node layer 612 (with node values x(n−1)) and a posterior node layer 614 (with node values x(n)). In particular, a pooling layer 613 can be characterized by the structure and the weights of the edges and the activation function forming a pooling operation based on a non-linear pooling function f. For example, in the two-dimensional case the values x(n) of the nodes 624 of the posterior node layer 614 can be calculated based on the values x(n−1) of the nodes 622 of the anterior node layer 612 as $$x^{(n)_b}[i, j] = f\left(x^{(n-1)}[id_1, jd_2], \ldots , x^{(n-1)_b}[(i+1)d_1 - 1, (j+1)d_2 - 1]\right)$$

In other words, by using a pooling layer 613 the number of nodes 622, 624 can be reduced, by re-placing a number d1·d2 of neighboring nodes 622 in the anterior node layer 612 with a single node 622 in the posterior node layer 614 being calculated as a function of the values of said number of neighboring nodes. In particular, the pooling function f can be the max-function, the average or the L2-Norm. In particular, for a pooling layer 613 the weights of the incoming edges are fixed and are not modified by training.

The advantage of using a pooling layer 613 is that the number of nodes 622, 624 and the number of parameters is reduced. This leads to the amount of computation in the network being reduced and to a control of overfitting.

In the displayed embodiment, the pooling layer 613 is a max-pooling layer, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

In general, the last layers of a convolutional neural network 600 are fully connected layers 615. A fully connected layer 615 is a connection layer between an anterior node layer 614 and a posterior node layer 616. A fully connected layer 613 can be characterized by the fact that a majority, in particular, all edges between nodes 614 of the anterior node layer 614 and the nodes 616 of the posterior node layer are present, and wherein the weight of each of these edges can be adjusted individually.

In this embodiment, the nodes 624 of the anterior node layer 614 of the fully connected layer 615 are displayed both as two-dimensional matrices, and additionally as non-related nodes (indicated as a line of nodes, wherein the number of nodes was reduced for a better presentability). This operation is also denoted as "flattening". In this embodiment, the number of nodes 626 in the posterior node layer 616 of the fully connected layer 615 smaller than the number of nodes 624 in the anterior node layer 614. Alternatively, the number of nodes 626 can be equal or larger.

Furthermore, in this embodiment the Softmax activation function is used within the fully connected layer 615. By applying the Softmax function, the sum the values of all nodes 626 of the output layer 616 is 1, and all values of all nodes 626 of the output layer 616 are real numbers between 0 and 1. In particular, if using the convolutional neural network 600 for categorizing input data, the values of the output layer 616 can be interpreted as the probability of the input data falling into one of the different categories.

In particular, convolutional neural networks 600 can be trained based on the backpropagation algorithm. For preventing overfitting, methods of regularization can be used, e.g., dropout of nodes 620, . . . , 624, stochastic pooling, use of artificial data, weight decay based on the L1 or the L2 norm, or max norm constraints.

According to an aspect, the machine learning model may comprise one or more residual networks (ResNet). In particular, a ResNet is an artificial neural network comprising at least one jump or skip connection used to jump over at least one layer of the artificial neural network. In particular, a ResNet may be a convolutional neural network comprising one or more skip connections respectively skipping one or more convolutional layers. According to some examples, the ResNets may be represented as m-layer ResNets, where m is the number of layers in the corresponding architecture and, according to some examples, may take values of 34, 50, 101, or 152. According to some examples, such an m-layer ResNet may respectively comprise (m−2)/2 skip connections.

A skip connection may be seen as a bypass which directly feeds the output of one preceding layer over one or more bypassed layers to a layer succeeding the one or more bypassed layers. Instead of having to directly fit a desired mapping, the bypassed layers would then have to fit a residual mapping "balancing" the directly fed output.

Fitting the residual mapping is computationally easier to optimize than the directed mapping. What is more, this alleviates the problem of vanishing/exploding gradients during optimization upon training the machine learning models: if a bypassed layer runs into such problems, its contribution may be skipped by regularization of the directly fed output. Using ResNets thus brings about the advantage that much deeper networks may be trained.

In particular, a recurrent machine learning model is a machine learning model whose output does not only depend on the input value and the parameters of the machine learning model adapted by the training process, but also on a hidden state vector, wherein the hidden state vector is based on previous inputs used on for the recurrent machine learning model. In particular, the recurrent machine learning model can comprise additional storage states or additional structures that incorporate time delays or comprise feedback loops.

In particular, the underlying structure of a recurrent machine learning model can be a neural network, which can be denoted as recurrent neural network. Such a recurrent neural network can be described as an artificial neural network where connections between nodes form a directed graph along a temporal sequence. In particular, a recurrent neural network can be interpreted as directed acyclic graph. In particular, the recurrent neural network can be a finite impulse recurrent neural network or an infinite impulse recurrent neural network (wherein a finite impulse network can be unrolled and replaced with a strictly feedforward neural network, and an infinite impulse network cannot be unrolled and replaced with a strictly feedforward neural network).

In particular, training a recurrent neural network can be based on the BPTT algorithm (acronym for "backpropagation through time"), on the RTRL algorithm (acronym for "real-time recurrent learning") and/or on genetic algorithms.

By using a recurrent machine learning model input data comprising sequences of variable length can be used. In particular, this implies that the method cannot be used only for a fixed number of input datasets (and needs to be trained differently for every other number of input datasets used as input), but can be used for an arbitrary number of input datasets. This implies that the whole set of training data, independent of the number of input datasets contained in different sequences, can be used within the training, and that training data is not reduced to training data corresponding to a certain number of successive input datasets.

FIG. 7 shows the schematic structure of a recurrent machine learning model F, both in a recurrent representation 702 and in an unfolded representation 704, that may be used to implement one or more machine learning models described herein. The recurrent machine learning model takes as input several input datasets x, $x_1, \ldots, x_N$ 706 and creates a corresponding set of output datasets y, $y_1, \ldots, y_N$ 708. Furthermore, the output depends on a so-called hidden vector h, $h_1, \ldots, h_N$ 710, which implicitly comprises information about input datasets previously used as input for the recurrent machine learning model F 712. By using these hidden vectors h, $h_1, \ldots, h_N$ 710, a sequentiality of the input datasets can be leveraged.

In a single step of the processing, the recurrent machine learning model F 712 takes as input the hidden vector $h_{n-1}$ created within the previous step and an input dataset $x_n$. Within this step, the recurrent machine learning model F generates as output an updated hidden vector $h_n$ and an output dataset $y_n$. In other words, one step of processing calculates $(y_n, h_n)=F(x_n, h_{n-1})$, or by splitting the recurrent machine learning model F 712 into a part F(y) calculating the output data and F(h) calculating the hidden vector, one step of processing calculates $y_n=F^{(y)}(x_n, h_{n-1})$ and $h_n=F^{(h)}(x_n, h_{n-1})$. For the first processing step, $h_0$ can be chosen randomly or filled with all entries being zero. The parameters of the recurrent machine learning model F 712 that were trained based on training datasets before do not change between the different processing steps.

In particular, the output data and the hidden vector of a processing step depend on all the previous input datasets used in the previous steps. $y_n=F^{(y)}(x_n, F^{(h)}(x_{n-1}, h_{n-2}))$ and $h_n=F(h)(x_n, F^{(h)}(x_{n-1}, h_{n-2}))$.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatuses, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatuses, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-4. Certain steps or functions of the methods and workflows described herein, including one or more of the steps or functions of FIGS. 1-4, may be performed by a server or by another processor in a network-based cloud-computing system. Certain steps or functions of the methods and workflows described herein, including one or more of the steps of FIGS. 1-4, may be performed by a client computer in a network-based cloud computing system. The steps or functions of the methods and workflows described herein, including one or more of the steps of FIGS. 1-4, may be performed by a server and/or by a client computer in a network-based cloud computing system, in any combination.

Systems, apparatuses, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 8:
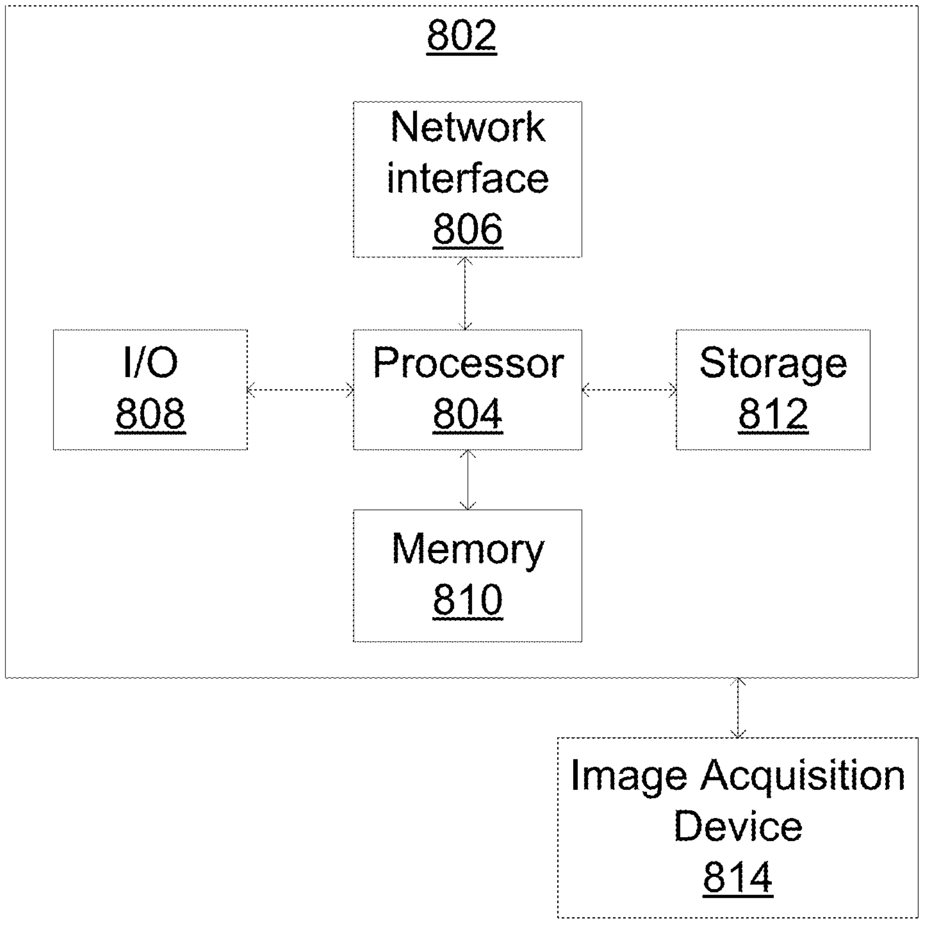
FIG. 8 shows a high-level block diagram of a computer that may be used to implement one or more embodiments.

A high-level block diagram of an example computer 802 that may be used to implement systems, apparatuses, and methods described herein is depicted in FIG. 8. Computer 802 includes a processor 804 operatively coupled to a data storage device 812 and a memory 810. Processor 804 controls the overall operation of computer 802 by executing computer program instructions that define such operations. The computer program instructions may be stored in data storage device 812, or other computer readable medium, and loaded into memory 810 when execution of the computer program instructions is desired. Thus, the method and workflow steps or functions of FIGS. 1-4 can be defined by the computer program instructions stored in memory 810 and/or data storage device 812 and controlled by processor 804 executing the computer program instructions. For example, the computer program instructions can be implemented as computer executable code programmed by one skilled in the art to perform the method and workflow steps or functions of FIGS. 1-4. Accordingly, by executing the computer program instructions, the processor 804 executes the method and workflow steps or functions of FIGS. 1-4. Computer 802 may also include one or more network interfaces 806 for communicating with other devices via a network. Computer 802 may also include one or more input/output devices 808 that enable user interaction with computer 802 (e.g., display, keyboard, mouse, speakers, buttons, etc.).

Processor 804 may include both general and special purpose microprocessors, and may be the sole processor or one of multiple processors of computer 802. Processor 804 may include one or more central processing units (CPUs), for example. Processor 804, data storage device 812, and/or memory 810 may include, be supplemented by, or incorporated in, one or more application-specific integrated circuits (ASICs) and/or one or more field programmable gate arrays (FPGAs).

Data storage device 812 and memory 810 each include a tangible non-transitory computer readable storage medium. Data storage device 812, and memory 810, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 808 may include peripherals, such as a printer, scanner, display screen, etc. For example, input/output devices 808 may include a display device such as a cathode ray tube (CRT) or liquid crystal display (LCD) monitor for displaying information to the user, a keyboard, and a pointing device such as a mouse or a trackball by which the user can provide input to computer 802.

An image acquisition device 814 can be connected to the computer 802 to input image data (e.g., medical images) to the computer 802. It is possible to implement the image acquisition device 814 and the computer 802 as one device. It is also possible that the image acquisition device 814 and the computer 802 communicate wirelessly through a network. In a possible embodiment, the computer 802 can be located remotely with respect to the image acquisition device 814.

Any or all of the systems, apparatuses, and methods discussed herein may be implemented using one or more computers such as computer 802.

One skilled in the art will recognize that an implementation of an actual computer or computer system may have other structures and may contain other components as well, and that FIG. 8 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving patient data; using a GMAI (generalist medical artificial intelligence) system, 1) performing a medical analysis task on the patient data and 2) determining an uncertainty associated with results of the medical analysis task performed using the GMAI system; determining whether the uncertainty associated with the results of the medical analysis task performed using the GMAI system is satisfactory; in response to determining that the uncertainty associated with the results of the medical analysis task performed using the GMAI system is not satisfactory, performing the medical analysis task on the patient data using an SMAI (specialist medical artificial intelligence) system; and outputting results of the medical analysis task performed using the SMAI system.

Illustrative embodiment 2. The computer-implemented method of illustrative embodiment 1, wherein determining whether the uncertainty associated with the results of the medical analysis task performed using the GMAI system is satisfactory comprises: comparing the uncertainty to one or more threshold values; and determining whether the uncertainty is satisfactory based on the comparison.

Illustrative embodiment 3. The computer-implemented method of any one of illustrative embodiments 1-2, wherein determining whether the uncertainty associated with the results of the medical analysis task performed using the GMAI system is satisfactory comprises: determining whether the uncertainty associated with the results of the medical analysis task performed using the GMAI system is satisfactory using a lookup table.

Illustrative embodiment 4. The computer-implemented method of any one of illustrative embodiments 1-3, further comprising receiving a prompt comprising instructions for performing the medical analysis task, wherein using a GMAI (generalist medical artificial intelligence) system, 1) performing a medical analysis task on the patient data and 2) determining an uncertainty associated with results of the medical analysis task performed using the GMAI system comprises: performing the medical analysis task on the patient data using the GMAI system based on the prompt.

Illustrative embodiment 5. The computer-implemented method of any one of illustrative embodiments 1-4, further comprising: in response to determining that the results of the medical analysis task performed by the GMAI system is satisfactory, outputting the results of the medical analysis task performed by the GMAI system.

Illustrative embodiment 6. The computer-implemented method of any one of illustrative embodiments 1-5, wherein the patient data comprises a current imaging study and a prior imaging study and the medical analysis task comprises analyzing changes between the current imaging study and the prior imaging study.

Illustrative embodiment 7. The computer-implemented method of any one of illustrative embodiments 1-6, wherein the GMAI system comprises a language model.

Illustrative embodiment 8. The computer-implemented method of any one of illustrative embodiments 1-7, wherein the medical analysis task comprises detection of nodules in a chest x-ray image.

Illustrative embodiment 9. The computer-implemented method of any one of illustrative embodiments 1-8, wherein the patient data comprises one or more medical images and text-based data.

Illustrative embodiment 10. An apparatus comprising: means for receiving patient data; means for, using a GMAI (generalist medical artificial intelligence) system, 1) performing a medical analysis task on the patient data and 2) determining an uncertainty associated with results of the medical analysis task performed using the GMAI system; means for determining whether the uncertainty associated with the results of the medical analysis task performed using the GMAI system is satisfactory; in response to determining that the uncertainty associated with the results of the medical analysis task performed using the GMAI system is not satisfactory, means for performing the medical analysis task on the patient data using an SMAI (specialist medical artificial intelligence) system; and means for outputting results of the medical analysis task performed using the SMAI system.

Illustrative embodiment 11. The apparatus of illustrative embodiment 10, wherein the means for determining whether the uncertainty associated with the results of the medical analysis task performed using the GMAI system is satisfactory comprises: means for comparing the uncertainty to one or more threshold values; and means for determining whether the uncertainty is satisfactory based on the comparison.

Illustrative embodiment 12. The apparatus of any one of illustrative embodiments 10-11, wherein the means for determining whether the uncertainty associated with the results of the medical analysis task performed using the GMAI system is satisfactory comprises: means for determining whether the uncertainty associated with the results of the medical analysis task performed using the GMAI system is satisfactory using a lookup table.

Illustrative embodiment 13. The apparatus of any one of illustrative embodiments 10-12, further comprising means for receiving a prompt comprising instructions for performing the medical analysis task, wherein the means for, using a GMAI (generalist medical artificial intelligence) system, 1) performing a medical analysis task on the patient data and 2) determining an uncertainty associated with results of the medical analysis task performed using the GMAI system comprises: means for performing the medical analysis task on the patient data using the GMAI system based on the prompt.

Illustrative embodiment 14. The apparatus of any one of illustrative embodiments 10-13, further comprising: in response to determining that the results of the medical analysis task performed by the GMAI system is satisfactory, means for outputting the results of the medical analysis task performed by the GMAI system.

Illustrative embodiment 15. A non-transitory computer-readable storage medium comprising instructions which, when executed by a computer, cause the computer to carry out operations comprising: receiving patient data; using a GMAI (generalist medical artificial intelligence) system, 1) performing a medical analysis task on the patient data and 2) determining an uncertainty associated with results of the medical analysis task performed using the GMAI system; determining whether the uncertainty associated with the results of the medical analysis task performed using the GMAI system is satisfactory; in response to determining that the uncertainty associated with the results of the medical analysis task performed using the GMAI system is not satisfactory, performing the medical analysis task on the patient data using an SMAI (specialist medical artificial intelligence) system; and outputting results of the medical analysis task performed using the SMAI system.

Illustrative embodiment 16. The non-transitory computer-readable storage medium of illustrative embodiment 15, wherein determining whether the uncertainty associated with the results of the medical analysis task performed using the GMAI system is satisfactory comprises: comparing the uncertainty to one or more threshold values; and determining whether the uncertainty is satisfactory based on the comparison.

Illustrative embodiment 17. The non-transitory computer-readable storage medium of any one of illustrative embodiments 15-16, wherein the patient data comprises a current imaging study and a prior imaging study and the medical analysis task comprises analyzing changes between the current imaging study and the prior imaging study.

Illustrative embodiment 18. The non-transitory computer-readable storage medium of any one of illustrative embodiments 15-17, wherein the GMAI system comprises a language model.

Illustrative embodiment 19. The non-transitory computer-readable storage medium of any one of illustrative embodiments 15-18, wherein the medical analysis task comprises detection of nodules in a chest x-ray image.

Illustrative embodiment 20. The non-transitory computer-readable storage medium of any one of illustrative embodiments 15-19, wherein the patient data comprises one or more medical images and text-based data.

The invention claimed is:

1. A computer-implemented method comprising:

training a GMAI (generalist medical artificial intelligence) system to perform a plurality of medical analysis tasks across a plurality of medical domains using training images and corresponding text-based data;

training an SMAI (specialist medical artificial intelligence) system to perform a specific medical analysis task using training data that is out-of-distribution of the training images and the corresponding text-based data on which the GMAI is trained;

receiving patient data;

using the GMAI system, 1) performing the specific medical analysis task on the patient data and 2) determining an uncertainty associated with results of the specific medical analysis task performed using the GMAI system;

determining whether the uncertainty associated with the results of the specific medical analysis task performed using the GMAI system is satisfactory;

in response to determining that the uncertainty associated with the results of the specific medical analysis task performed by the GMAI system is satisfactory, outputting the results of the specific medical analysis task performed using the GMAI system; and in response to determining that the uncertainty associated with the results of the specific medical analysis task performed using the GMAI system is not satisfactory:

performing the specific medical analysis task on the patient data using the SMAI system; and outputting results of the specific medical analysis task performed using the SMAI system.

2. The computer-implemented method of claim 1, wherein determining whether the uncertainty associated with the results of the specific medical analysis task performed using the GMAI system is satisfactory comprises:

comparing the uncertainty to one or more threshold values; and determining whether the uncertainty is satisfactory based on the comparison.

3. The computer-implemented method of claim 1, wherein determining whether the uncertainty associated with the results of the specific medical analysis task performed using the GMAI system is satisfactory comprises:

determining whether the uncertainty associated with the results of the specific medical analysis task performed using the GMAI system is satisfactory using a lookup table.

4. The computer-implemented method of claim 1, further comprising receiving a prompt comprising instructions for performing the specific medical analysis task, wherein using the GMAI system, 1) performing the specific medical analysis task on the patient data and 2) determining an uncertainty associated with results of the specific medical analysis task performed using the GMAI system comprises:

performing the specific medical analysis task on the patient data using the GMAI system based on the prompt.

5. The computer-implemented method of claim 1, wherein the patient data comprises a current imaging study and a prior imaging study and the specific medical analysis task comprises analyzing changes between the current imaging study and the prior imaging study.

6. The computer-implemented method of claim 1, wherein the GMAI system comprises a language model.

7. The computer-implemented method of claim 1, wherein the medical analysis task comprises detection of nodules in a chest x-ray image.

8. The computer-implemented method of claim 1, wherein the patient data comprises one or more medical images and text-based data.

9. An apparatus comprising:

means for training a GMAI (generalist medical artificial intelligence) system to perform a plurality of medical analysis tasks across a plurality of medical domains using training images and corresponding text-based data;

means for training an SMAI (specialist medical artificial intelligence) system to perform a specific medical analysis task using training data that is out-of-distribution of the training images and the corresponding text-based data on which the GMAI is trained;

means for receiving patient data;

means for, using the GMAI system, 1) performing the specific medical analysis task on the patient data and 2) determining an uncertainty associated with results of the specific medical analysis task performed using the GMAI system;

means for determining whether the uncertainty associated with the results of the specific medical analysis task performed using the GMAI system is satisfactory;

in response to determining that the uncertainty associated with the results of the specific medical analysis task performed by the GMAI system is satisfactory, outputting the results of the specific medical analysis task performed using the GMAI system; and in response to determining that the uncertainty associated with the results of the specific medical analysis task performed using the GMAI system is not satisfactory:

means for performing the specific medical analysis task on the patient data using the SMAI system; and means for outputting results of the specific medical analysis task performed using the SMAI system.

10. The apparatus of claim 9, wherein the means for determining whether the uncertainty associated with the results of the specific medical analysis task performed using the GMAI system is satisfactory comprises:

means for comparing the uncertainty to one or more threshold values; and means for determining whether the uncertainty is satisfactory based on the comparison.

11. The apparatus of claim 9, wherein the means for determining whether the uncertainty associated with the results of the specific medical analysis task performed using the GMAI system is satisfactory comprises:

means for determining whether the uncertainty associated with the results of the specific medical analysis task performed using the GMAI system is satisfactory using a lookup table.

12. The apparatus of claim 9, further comprising means for receiving a prompt comprising instructions for performing the specific medical analysis task, wherein the means for, using the GMAI system, 1) performing the specific medical analysis task on the patient data and 2) determining an uncertainty associated with results of the specific medical analysis task performed using the GMAI system comprises:

means for performing the specific medical analysis task on the patient data using the GMAI system based on the prompt.

13. A non-transitory computer-readable storage medium comprising instructions which, when executed by a computer, cause the computer to carry out operations comprising:

training a GMAI (generalist medical artificial intelligence) system to perform a plurality of medical analysis tasks across a plurality of medical domains using training images and corresponding text-based data;

training an SMAI (specialist medical artificial intelligence) system to perform a specific medical analysis task using training data that is out-of-distribution of the training images and the corresponding text-based data on which the GMAI is trained;

receiving patient data;

using the GMAI system, 1) performing the specific medical analysis task on the patient data and 2) determining an uncertainty associated with results of the specific medical analysis task performed using the GMAI system;

determining whether the uncertainty associated with the results of the specific medical analysis task performed using the GMAI system is satisfactory;

in response to determining that the uncertainty associated with the results of the specific medical analysis task performed by the GMAI system is satisfactory, outputting the results of the specific medical analysis task performed using the GMAI system; and in response to determining that the uncertainty associated with the results of the specific medical analysis task performed using the GMAI system is not satisfactory:

performing the specific medical analysis task on the patient data using the SMAI system; and outputting results of the specific medical analysis task performed using the SMAI system.

14. The non-transitory computer-readable storage medium of claim 13, wherein determining whether the uncertainty associated with the results of the specific medical analysis task performed using the GMAI system is satisfactory comprises:

comparing the uncertainty to one or more threshold values; and determining whether the uncertainty is satisfactory based on the comparison.

15. The non-transitory computer-readable storage medium of claim 13, wherein the patient data comprises a current imaging study and a prior imaging study and the medical analysis task comprises analyzing changes between the current imaging study and the prior imaging study.

16. The non-transitory computer-readable storage medium of claim 13, wherein the GMAI system comprises a language model.

17. The non-transitory computer-readable storage medium of claim 13, wherein the medical analysis task comprises detection of nodules in a chest x-ray image.

18. The non-transitory computer-readable storage medium of claim 13, wherein the patient data comprises one or more medical images and text-based data.

* * * * *